United States Patent [19]

Fenske et al.

[11] Patent Number: 4,810,828
[45] Date of Patent: Mar. 7, 1989

[54] ANTI-INFLAMMATORY IMIDAZOLE COMPOUNDS

[75] Inventors: Dankwart C. Fenske, Weybridge; Elizabeth A. Kuo, Covingham; Wilfred R. Tully, Cirencester, all of Great Britain

[73] Assignee: Roussel Uclaf, Paris, France

[21] Appl. No.: 80,407

[22] Filed: Jul. 31, 1987

[30] Foreign Application Priority Data

Aug. 18, 1986 [GB] United Kingdom ............... 8620060

[51] Int. Cl.$^4$ .................. A61K 31/415; C07D 233/84
[52] U.S. Cl. .................................. 514/398; 514/392; 514/400; 548/321; 548/337; 548/343
[58] Field of Search ............... 548/337, 343; 514/398, 514/400

[56] References Cited

PUBLICATIONS

*Chemical Abstracts*, 101:55097w (1984) [EP 104,104, Tully, 3/28/84].

*Primary Examiner*—Richard A. Schwartz
*Attorney, Agent, or Firm*—Bierman and Muserlian

[57] ABSTRACT

A compound selected from the group consisting of a compound of the formula

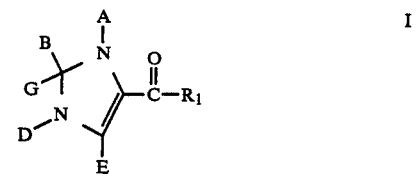

wherein $R_1$ is selected from the group consisting of

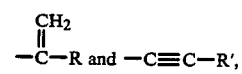

and the remaining substituents are as defined hereinbelow and its non-toxic, pharmaceutically acceptable acid addition salts having anti-inflammatory activity and their preparation.

12 Claims, No Drawings

ANTI-INFLAMMATORY IMIDAZOLE COMPOUNDS

OBJECTS OF THE INVENTION

It is an object of the invention to provide the novel compounds of formula I and their non-toxic, pharmaceutically acceptable acid addition salts and their preparation.

It is another object of the invention to provide novel anti-inflammatory compositions and a novel method of treating inflammation in warm-blooded animals.

These and other objects and advantages of the invention will become obvious from the following detailed description.

THE INVENTION

The novel compounds of the invention are selected from the group consisting of a compound of the formula

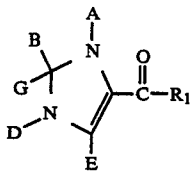

wherein $R_1$ is selected from the group consisting of

R is selected from the group consisting of hydrogen and alkyl of 1 to 5 carbon atoms, R' is selected from the group consisting of hydrogen, alkyl and hydroxyalkyl of 1 to 5 carbon atoms, and aryl of 6 to 10 carbon atoms optionally substituted with at least one member of the group consisting of halogen, —OH, —COOH, CF$_3$ and alkyl and alkoxy of 1 to 5 carbon atoms, (a) A is alkyl of 1 to 5 carbon atoms, B and G together with the carbon atom to which they are attached are carbonyl or thiocarbonyl and D is selected from the group consisting of alkyl of 1 to 5 carbon atoms and phenyl optionally substituted with at least one member of the group consisting of halogen, —OH, —COOH, —CF$_3$ and alkyl and alkoxy of 1 to 5 carbon atoms or (b) A and B together form a bond, G is selected from the group consisting of alkyl, alkoxy and alkylthio of 1 to 5 carbon atoms and alkylsulfinyl and alkylsulfonyl of 1 to 5 carbon atoms and D is selected from the group consisting of alkyl of 1 to 5 carbon atoms and phenyl optionally substituted with at least one member of the group consisting of halogen, —OH, —COOH, —CF$_3$ and alkyl and alkoxy of 1 to 5 carbon atoms or (c) A and B together form a bond, G and D together form a member of the group consisting of

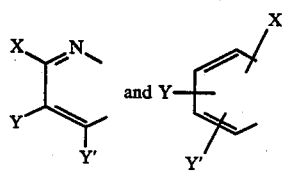

wherein X is alkoxy or alkylthio of 1 to 5 carbon atoms, Y and Y' are individually hydrogen or alkyl of 1 to 5 carbon atoms and E is hydrogen or halogen with the proviso when A and B are a bond and G and D together are

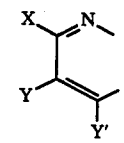

and $R_1$ is

E is other than hydrogen and its non-toxic, pharmaceutically acceptable acid addition salts.

When A and B together form a bond and G and D together form

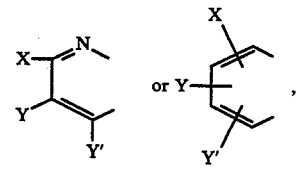

the compounds of formula I may have the formula

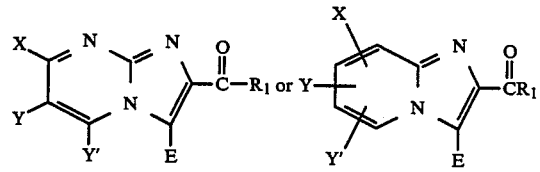

respectively.

Examples of alkyl and alkoxy of 1 to 5 carbon atoms are methyl, ethyl, isopropyl, n-propyl and linear and branched butyl and pentyl, methoxy, ethoxy, isopropoxy, n-propoxy and linear and branched butoxy and pentyloxy. Examples of hydroxyalkyl of 1 to 5 carbon atoms are hydroxymethyl, hydroxyethyl, hydroxy-n-propyl, hydroxyisopropyl and linear or branched hydroxybutyl and hydroxypentyl.

Examples of aryl 6 to 10 carbon atoms are phenyl and naphthyl optionally substituted as discussed above. Examples of alkylthio of 1 to 5 alkyl carbon atoms are methylthio, ethylthio, n-propylthio, isopropylthio and linear and branched butylthio and pentylthio. Examples of alkylsulfinyl and alkylsulfonyl of 1 to 5 alkyl carbon atoms are methylsulfinyl, ethylsulfinyl, n-propylsulfinyl, isopropylsulfinyl, linear and branched butylsulfinyl and pentylsulfinyl, methylsulfonyl, ethylsulfonyl, isopropylsulfonyl, n-propylsulfonyl and linear and branched butylsulfonyl and pentylsulfonyl.

Examples of suitable acids for the formation of the non-toxic, pharmaceutically acceptable acid addition salts are inorganic acids such as hydrochloric acid, hydrobromic acid hydriodic acid, nitric acid, sulfuric acid and phosphoric acid and organic acids such as propionic acid, formic acid, benzoic acid, maleic acid, fumaric acid, succinic acid, tartaric acid, citric acid, oxalic acid, glyoxylyic acid, aspartic acid, alkanesulfonic acids such as methanesulfonic acid, and arylsulfonic acid such as benzenesulfonic acids.

Examples of preferred compounds of formula I are those wherein $R_1$ is

and E is halogen, those wherein $R^1$ is —C≡C—R' and E is halogen, those wherein A and B together are a bond, G and D together are

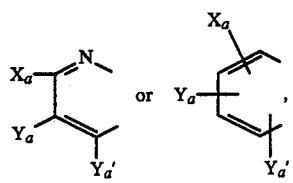

E is halogen, $X_a$ is methoxy or methylthio and $Y_a$ and $Y_a'$ are individually hydrogen, methyl or ethyl and E is halogen and those wherein A and B together are a bond, G is alkylthio of 1 to 5 carbon atoms and D is optionally substituted phenyl and their non-toxic, pharmaceutically acceptable acid addition salts.

Among the preferred compounds of formula I are
1-(3-bromo-6-ethyl-5-methyl-7-methylthioimidazo[1,2-a]-pyrimidin-2-yl)-2-methyl-2-propen-1-one;
1-[5-bromo-1-(4-ethylphenyl)-2-methylthioimidazol-4-yl]-2-methyl-2-propen-1-one;
1-[5-bromo-1-(4-methoxyphenyl)-2-methylthioimidazol-4-yl]-2-propen-1-one;
1-(3-bromo-6-ethyl-7-methoxy-5-methylimidazo[1,2-a]-pyrimidin-2-yl)-2-propen-1-one;
1-(3-bromo-6-ethyl-7-methoxy-5-methylimidazol[1,2-a]-pyrimidin-2-yl)-3-phenyl-2-propyn-1-one and their non-toxic, pharmaceutically acceptable acid addition salts.

The novel process of the invention for the preparation of compounds of formula I wherein E is hydrogen comprises oxidizing a compound of the formula

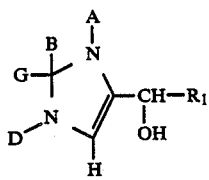

wherein B,G,D,A and $R_1$ are defined as above with an oxidizing agent such as manganese dioxide and optionally salifying the corresponding compound of formula I. The oxidation is preferably effected in an organic solvent such as chloroform at reflux.

The compounds of formula IV may be prepared by reacting a compound of the formula

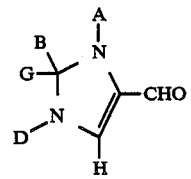

wherein A,B,G and D have the above definitions with a source of $R_1^-$ carbonions such as Grignard reagent of the formula $R_1MgBr$ III or an alkyllithium of the formula $R_1$-Li $III_A$ wherein $R_1$ has the above definition preferably in an inert organic solvent such as tetrahydrofuran.

A process for the preparation of compounds of formula $I_B$ wherein E is halogen

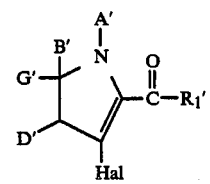

wherein Hal represents a halogen atom, $R_1'$ is

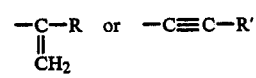

wherein R and R' have the above definitions and (a) A' is alkyl of 1 to 5 carbon atoms, B' and G' together with the carbon atom to which they are attached are carbonyl or thiocarbonyl and D' is alkyl of 1 to 5 carbon atoms or phenyl optionally substituted with at least one member of the group consisting of halogen, —OH, —COOH, —CF$_3$ and alkyl and alkoxy of 1 to 5 carbon atoms or (b) A' and B' together form a bond, G' is alkyl or alkylthio of 1 to 5 carbon atoms and D' is alkyl of 1 to 5 carbon atoms or phenyl optionally substituted with at least one member of the group consisting of halogen, —OH, —COOH, CF$_3$ and alkyl and alkoxy of 1 to 5 carbon atoms or (c) A' and B' are a bond, G' and D' together are

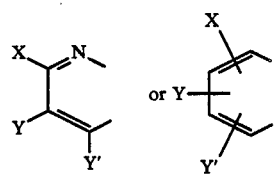

wherein X, Y and Y' are as defined above comprises reacting a compound of the formula

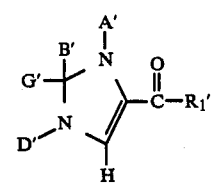

wherein A', B', G', D' and $R'_1$ are defined as above with a N-halosuccinimide optionally followed by salification of the compound of formula $I_B$. The reaction is preferably effected in an organic solvent such as chloroform or carbon tetrachloride.

A process for the preparation of a compound of the formula

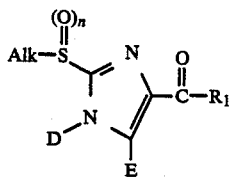

$I_D$ wherein $R_1$, D and E are defined as above, Alk is alkyl of 1 to 5 carbon atoms and n is 1 or 2 comprises oxidizing a compound of the formula

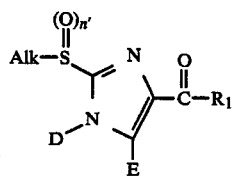

$I_C$ wherein D,E,$R_1$ and Alk have the above definition and n' is 0 or 1 with an oxidizing agent such as sodium metaperiodate to obtain the compound of formula $I_D$ which may be optionally salified. The reaction is preferably effected in a suitable organic solvent such as aqueous alkanol such as methanol and at a suitable temperature such as about 50° C.

To prepare the alkylsulfinyl derivatives, the compounds of formula $I_C$ wherein n' is 0 are reacted with one equivalent of oxidizing agent. The alkylsulfonyl compounds of formula $I_D$ wherein n is 2 may be prepared by oxidizing the compound of formula $I_C$ wherein n' is 0 with at least two equivalents of oxidizing agent or oxidize the compound of formula $I_C$ wherein n' is 1 with at least one equivalent of oxidizing agent.

A process for the preparation of the compounds of formula I wherein at least one of $R_1$ and D contains a hydroxy group comprises removing a protective group from a compound of the formula

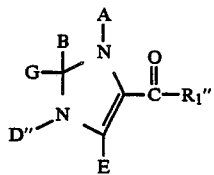

V wherein A, B, G and E have the above definitions, D'' is D or a precursor of a group D with a protected hydroxy and R''$_1$ is $R_1$ or a precursor of a group $R_1$ with a protected hydroxy, with the proviso that at least one of D'' and R''$_1$ is a precursor of a group containing a protected hydroxy. The compounds of formula V may be prepared by one of the previous processes using starting materials wherein $R_1$ and/or D contains protected hydroxy groups.

As will be appreciated from the above, certain of the compounds of the invention possess free hydroxy groups, and it may thus be necessary or desirable to protect any free hydroxy groups during the preparation of the said compounds. In such situations, the protecting group will remain in place throughout the duration of the process sequence, and will itself be removed by traditional methods (e.g. by hydrolysis) as the final step thereof.

For example, if R' is hydroxyalkyl of 1 to 5 carbon atoms, the protecting group used will conveniently be of the type customarily employed for the protection of aliphatic hydroxy groups such as tetrahydropyranyl, although other suitable protecting groups will be apparent to those skilled in the art. Thus, a compound of formula III or III$_A$ wherein R' of $R_1$ is a suitably protected hydroxyalkyl of 1 to 5 carbon atoms will be taken and reacted with the appropriate compound of formula II. The protected derivative of formula IV thereby obtained may then be elaborated as appropriate according to one or more of processes (A) to (C) above, the protecting group on the hydroxy substituent being retained for the remaining steps of the synthetic sequence, its removal consituting the final step thereof. Such a process is described in Examples 22 and 23.

Similarly, in those cases wherein R' is hydroxy-substituted aryl of 6 to 10 carbon atoms and/or D is a hydroxy-substituted phenyl, the protecting group used will conveniently be of the type customarily employed for the protection of aromatic hydroxys, a typical example being benzyl although as before other suitable protecting groups will be apparent to those skilled in the art. Again, the protected derivative of formula IV involved as an intermediate in the synthetic sequence may be elaborated as appropriate according to one or more of processes (A) to (C) above. As before, the protecting group on the hydroxy will be retained for the remaining steps of the synthetic sequence and its removal will constitute the final step thereof and such a process is described in Example 14.

The compounds are basic in character and their acid addition salts may be obtained by reacting approximately stoichiometric amounts of the compound of formula I and the appropriate acid in a suitable solvent with or without isolation of the compound of formula I The novel anti-inflammatory compositions of the invention are comprised of an anti-inflammatory effective amount of at least one compound of formula I and their non-toxic, pharmaceutically acceptable acid addition salts and an inert pharmaceutical carrier or excipient. The compositions may be in the form of tablets, dragees, capsules, powders, suppositories, aerosols and injectable solutions or suspensions.

Examples of suitable excipients are talc, gum arabic, lactose, starch, magnesium stearate, cocoa butter, aqueous or nonaqueous vehicles, animal or vegetable fats, paraffin derivatives, glycols, various wetting, dispersing or emulsfying agents and/or preservatives.

The compositions of the invention possess very interesting pharmacological properties; particularly they have been found to possess an anti-inflammatory effect, notably in their ability to moderate inflammatory/immune cell function by restricting arachiodonic acid release and consequential eicosanoid biosynthesis. They are useful for the treatment of inflammatory and immunological disorders such as rheumatoid arthritis, osteoarthritis and psoriasis. The preferred active ingredients are as indicated above.

The novel method of the invention for treating inflammation in warm-blooded animals, including humans, comprises administering to warm-blooded animals an anti-inflammatorily effective amount of at least one compound of formula I and their non-toxic, pharmaceutically acceptable acid addition salts. The compounds may be administered orally, rectally or parenterally and the usual daily dose in 0.001 to 2.5 mg/kd depending on the conditions treated, the specific compound and method of administration.

Imidazole-4-carboxaldehydes of formula II may be prepared by a modification of the procedures described in Helv. Chim. Acta. 1960, Vol. 43, p. 1787 and Tetrahedron, 1963, Vol. 19, p. 1883. An example of such a preparation is given below as Preparation A.

Imadazo[1,2-a]pyrimidine-2-carboxaldehydes of formula II may be prepared as in British patent application No. 2,128,989 or by methods analogous thereto, as also may compounds of formula I$_A$ wherein A' and B' together are a bond, G' and D' together are

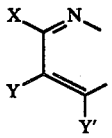

wherein X, Y, and Y' are as defined above and

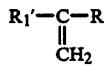

in which R is as defined above which, while not themselves being compounds of the invention, are nevertheless useful intermediates for the compounds of formula I$_B$. An example of such a preparation is described in Preparation H below.

Imidazol[1,2-a]pyridine-2-carboxaldehydes of formula II may conveniently be prepared using a variant of the process described in British patent application No. 2,128,989 from the corresponding imidazo[1,2-a]pyridine-2-carboxylate esters which, in turn, may themselves be obtained by the method detailed in J. Org. Chem., 1965, Vol. 30, p. 2403.

In the following examples there are described several preferred embodiments to illustrate the invention. However, it is to be understood that the invention is not intended to be limited to the specific embodiments.

Preparation A 1-(4-methoxyphenyl)-2-methylthioimidazole-4-carboxaldehyde

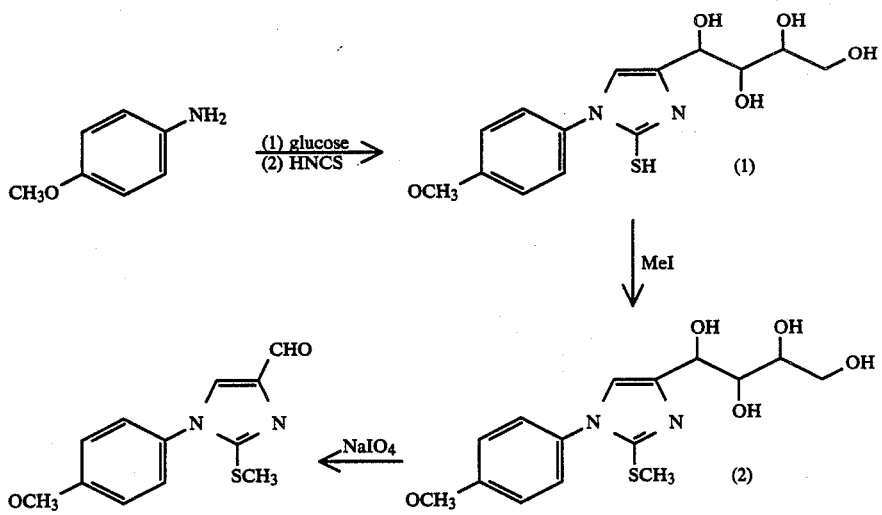

Step (a):

A mixture of 18 g of glucose, 12.3 of p-methoxyaniline, 36 ml of water and 1 ml of acetic acid was heated on a steam-bath for 15 minutes after which time a clear solution was formed. 7.6 g of ammonium isothiocyanate and 6 g of acetic acid were added and the solution was heated on a steam-bath for 2 hours after which time solidification occurred. The solid was digested with hot water, filtered, stirred in methanol for 1 hour, filtered, washed with ether and dried to obtain 10.5 g (32%) of intermediate (1) melting at 215°–6° C. (Tetrahedron, 1963, Vol. 19, page 1883, m.p. 215°–6° C.)

Step (b):

A mixture of 10.5 g of intermediate (1) 5.0 g of iodomethane and 5.0 g of potassium carbonate was stirred in 50 ml of dimethylformamide for 1 hour and then was diluted with water to crystallize 7.6 g (69%) of intermediate (2) as a brown solid which was used directly in the next step.

Step (c):

A mixture of 7.6 g of intermediate (2) and 16.0 g of sodium metaperiodate was stirred in 100 ml of aqueous methanol of 10% for 1 hour. The solution was concentrated under reduced pressure and diluted with water to crystallize 2.7 g of aldehyde (3) (49% yield) as colorless crystals after crystallization from ethanol melting at 118°–20° C.

Compounds B to E were prepared analogously. Compound F was prepared as described in published British patent application No. 2,128,989, and compound G was prepared by an analogous method. Compounds J and K were prepared as indicated in Example 1 Step A. The Yield, melting point and analytical data of starting compounds of formula II are given in Tables A and B. Yield, melting point and analytical data of intermediates of formula I$_A$ are given in Table C.

EXAMPLE 1

1-(3-bromo-6-ethyl-5-methyl-7-methylthio-imidazo[1,2-a]pyrimidin-2-yl)-2-methyl-2-propen-1-one

STEP A 1-(6-ethyl-5-methyl-7-methylthioimidazo[1,2-a]pyrimidin-2-yl)-2-methyl-2-propen-1-one (Method A)

1.2 g (4.78 mmol) of 6-ethyl-5-methyl-7-methylthioimidazo[1,2-a]pyrimidine-2-carboxaldehyde were added to a solution of 7.17 mmol of 2-propenyl magnesium bromide in 50 ml of dry tetrahydrofuran under nitrogen and the mixture was stirred at room temperature for 3 hours. The reaction mixture was quenched with aqueous ammonium chloride and was extracted with chloroform (3×50 ml). The organic layer was dried over $MgSO_4$ and the solvent was removed under reduced pressure. The residual oil was purified by flash chromatography over 25 mg of silica, (dichloromethane:ethyl acetate 1:0 gradually changing to 0.1) to obtain 1.17 g (84%) of the 2-methyl-2-propen-1-ol as colorless crystals melting at 116°-8° C. $\nu_{Max}$ (KBr) 3160, 2960, 2920, 2870 and 1610 $cm^{-1}$.

A solution of 1.4 g (4.78 mmol) of 2-methyl-2-propen-1-ol in 200 ml of chloroform was heated under reflux with 5 g of manganese dioxide for 2 hours and then was filtered hot through celite. The solvent was removed under reduced pressure to obtain 1.25 g (90%) of 1-(6-ethyl-5-methyl-7-methylthioimidazol[1,2-a]pyrimidin-2-yl)-2-methyl-2-propen-1-one as yellow crystals melting at 136°-7° C. (from ethyl acetate).

STEP B 1-(3-bromo-6-ethyl-5-methyl-7-methylthioimidazo[1,2-a]pyrimidin-2-yl)-2-methyl-2-propen-1-one Method B A solution of 1.0 g (3.63 mmol) of 1-(6-ethyl-5-methyl-7-methylthioimidazo[1,2-a]pyrimidin-2-yl)-2-methyl-2-propen-1-one in 50 ml of chloroform was treated with 0.71 g (4.0 mmol) of N-bromosuccinimide. After 20 minutes at room temperature, the solvent was removed under reduced pressure and the residue was purified by flash chromatography (silica, 25 g: dichloromethane) to obtain 1.1 g (87%) of 1-(3-bromo-6-ethyl-5-methyl-7-methylthioimidazo[1,2-a]pyrimidin-2-yl)-2-methyl-2-propen-1-one in the form of pale yellow crystals melting at 87°-9° C.

EXAMPLES 2 TO 13

Using the procedure of Step A and/or Step B of Example 1, the compounds of Examples 2 to 13 were prepared.

EXAMPLE 2

(3-bromo 6-ethyl 7-methoxy 5-methylimidazo[1,2-a]pyrimidin-2-yl)isopropenyl methanone

EXAMPLE 3

(3-chloro 6-ethyl 7methoxy 5-methylimidazo[1,2-a]pyrimidin-2-yl)isopropenyl methanone

EXAMPLE 4

(7-methoxy 5-methylimidazo[1,2-a]pyrimidin-2-yl)ethenyl methanone

EXAMPLE 5

(3-bromo 6-ethyl 7-methoxy 5-methylimidazo[1,2-a]pyrimidin-2-yl)ethenyl methanone

EXAMPLE 6

[1-(4-ethylphenyl) 2-imidazol-4-yl]isopropenyl methanone

EXAMPLE 7

[1-(4-ethylphenyl) 5-bromo 2-thiomethylimidazol-4-yl]isopropenyl methanone

EXAMPLE 8

[1-(4-methoxyphenyl) 5-bromo 2-thiomethylimidazol-4-yl]isopropenyl methanone

EXAMPLE 9

[1-(4-methoxyphenyl) 5-chloro 2-thiomethylimidazol-4-yl]isopropenyl methanone

EXAMPLE 10

[1-(4-methylphenyl) 5-bromo 2-thiomethylimidazol-4-yl]isoproprnyl methanone

EXAMPLE 11

[1-(4-methylphenyl) 5-bromo 2-thioisopropylimidazol-4-yl]isopropenyl methanone

EXAMPLE 12

[1-(4-fluorophenyl) 5-bromo 2-thiomethylimidazol-4-yl]isopropenyl methanone

EXAMPLE 13

[1-(4-methoxyphenyl) 5-bromo 2-thiomethylimidazol-4-yl]ethenyl methanone

EXAMPLE 14

[5-bromo-1-(4-hydroxyphenyl)-2-methylthioimidazol-4-yl]-2-methyl-2-propen-1-one

STEP A 1-(4-benzyloxyphenyl)-2-methylthioimidazole-4-carboxaldehyde p-benzyloxyaniline was reacted according to method of preparation A to obtain 1-(4-benzyloxyphenyl)-2-methylthioimidazole-4-carboxaldehyde

STEP B

[1-(4-benzyloxyphenyl)-2-methylthioimidazol-4-yl]2-methyl-2-propen-1-one

The compound of Step A was reacted by the method of Step A of Example 1 to obtain [1-(4-benzyloxyphenyl)-2-methylthioimidazol-4-yl]-2-methyl-2-propen-1-one

STEP C

[1-(4-benzyloxyphenyl)-5-bromo-2-methylthioimidazol-4-yl]-2-methyl-2-propen-1-one The product of Step B was reacted by the method of Step B of Example 1 to obtain [1-(4-benzyloxyphenyl)-5-bromo-2-methylthioimidazol-4-yl]-2-methylI-2-propen-1-one.

STEP D

[5-bromo-1-(4-hydroxyphenyl)-2-methylthioimidazol-4-yl]2-methyl-2-propen-1-one 2.7 g (6.1 mmol) of [1-(4-benzyloxyphenyl)-5-bromo-2-methylthioimidazol-4-yl]-2-methyl-2-propen-1-one were heated for 24 hours at 30° C. in 25 ml of trifluoroacetic acid. Removal of trifluoroacetic acid was effected at 30° C. under reduced pressure followed by addition of iced water to obtain an oil which was extracted with ether and purified by flash chromatography on silica (5% ethyl acetate in petroleum ether) to obtain 1.9 g (88%) of [5-bromo-1-(4-hydroxyphenyl)-2-methylthioimidazol-4-yl]2-methyl-2-propen-1-one in the form of pale yellow crystals melting at 159°–161° C.

EXAMPLE 15

(1-ethyl 5-bromo 2-thioisopropyl imidazol-4-yl)isopropenyl methanone

Using the method of Example 1, the corresponding compound of formula $I_4$ was reacted to obtain the compound of Example 15.

EXAMPLE 16

[5-chloro-1-(4-ethylphenyl)-2-(prop-2-ylsulfinyl)-imidazol-4-yl]-2-methyl-2-propen-1-one A mixture of 3.0 g (8.6 mmol) of [5-chloro-1-(4-ethylphenyl)-2-(prop-2-ylthio)-imidazol-4-yl]-2-methyl-2-propen-1-one and 2.3 g (11 mmol) of sodium metaperiodate was heated at 50° C. for 3 hours in 30 ml of 90% aqueous methanol. The mixture was cooled and poured into water. Extraction with dichloromethane yielded an oil which was purified by flash chromatography on silica (20% ethyl acetate in petroleum ether) to obtain 1.3 g (41%) of [5-chloro-1-(4-ethylphenyl)-2-(prop-2-ylsulfinyl)-imidazol-4-yl]-2-methyl-2-propen-1-one as cream-colored crystals melting at 83°–4° C.

EXAMPLE 17

[1-(4-ethylphenyl)5-chloro 2-ethylsulfininylimidazol-4-yl]isopropenyl methanone

Using the method of Example 16, the corresponding compound of formula $I_C$ was reacted to obtain the compound of Example 17.

EXAMPLES 18 TO 21

Using the methods of Step A or B of Example 1, the corresponding compounds of formulae II or $I_4$ respectively were reacted to obtain the compounds of Examples 18 to 21.

EXAMPLE 18

(6-ethyl 7-methoxy 5-methylimidazo [1,2-a]pyrimidin-2-yl)phenylethynyl methanone

EXAMPLE 19

1-(6-ethyl 7-methoxy 5-methylimidazo[1,2-a]pyrimidin-2-yl) (3,3-dimethylbut-1-ynyl)methanone

EXAMPLE 20

(3-bromo 6-ethyl 7-methoxy 5-methylimidazo[1,2-a]pyrimidin-2-yl) (3,3-dimethylbut-1-ynyl)methanone

EXAMPLE 21

(3-bromo 6-ethyl 7-methoxy 5-methylimidazo[1,2-a]pyrimidin-2-yl) (2-phenylethy-1-yl)methanone

EXAMPLE 22

1-(3-bromo-6-ethyl-7-methoxy-5-methyl-imidazo[1,2-a]pyrimidin-2-yl)-4-hydroxy-2-butyn-1-one

STEP A 1-(6-ethyl-7-methoxy-5-methylimidazo[1,2-a]pyrimidin-2-yl)-4-(tetrahydropyran-2-yloxy)-2-butyn-1-one 6-ethyl-7-methoxy-5-methylimidazo[1,2-a]pyrimidin-2-carboxaldehyde and 3-(tetrahydropyran-2-yloxy)-1-propynyl-magnesium bromide [J. Chem. Soc., 1950, 3646] were reacted by the method of Step A of Example 1 to obtain 1-(6-ethyl-7-methoxy-5-methylimidazol[1,2-a]pyrimidin-2-yl)-4-(tetrahydropyran-2-yloxy)-2-butyn-1-one.

STEP B 1-(3-bromo-6-ethyl-7-methoxy-5-methylimidazo[1,2-a]pyrimidin-2-yl)-4-(tetrahydropyran-2-yloxy)-2-butyn-1-one The compound of Step A was reacted by the procedure of Step B of Example 1 to obtain 1-3-(bromo-6-ethyl-7-methoxy-5-methylimidazo[1,2-a]pyrimidin-2-yl)-4-(tetrahydropyran-2-yloxy)-2-butyn-1-one.

STEP C 1-(3-bromo-6-ethyl-7-methoxy-5-methylimidazo[1,2-a]pyrimidin-2-yl)-4-hydroxy-2-butyn-1-one A solution of 5.0 g (11.5 mmol) of 1-(3-bromo-6-ethyl-7-methoxy-5-methylimidazo[1,2-a]pyrimidin-2-yl)-4-(tetrahydropyran-2-yloxy)-2-butyn-1-one in a mixture of 100 ml of methanol and 35 ml of 2N hydrochloric acid stood at room temperature for 30 minutes and then was neutralized with aqueous sodium bicarbonate. Extraction with chloroform gave an oil which was chromatographed over silica (chloroform:ether:methanol 100:0:0 gradually changing to 0:95:5) to obtain 1.3 g (32%) of 1-(3-bromo-6-ethyl-7-methoxy-5-methylimidazo[1,2-a]pyrimidin-2-yl)-4-hydroxy-2-butyn-1-one as off-white crystals melting at 212°–3° C. (decomp.).

EXAMPLE 23

1-(6-ethyl-7-methoxy-5-methylimidazo[1,2-a]pyrimidin-2-yl)-4-hydroxy-2-butyn-1-one

STEP A 1-(6-ethyl-7-methoxy-5-methylimidazo[1,2-a]pyrimidin-2-yl)-4-(tetrahydropyran-2-yloxy)-2-butyn-1-one Using the procedure of Step A of Example 22, 1-(6-ethyl-7-methoxy-5-methylimidazo[1,2-a]pyrimidin-2-yl)-4-(tetrahydropyran-2-yloxy)-2-butyn-1-one was prepared.

STEP B 1-(6-ethyl-7-methoxy-5-methylimidazo[1,2-a]pyrimidin-2-yl)-4-hydroxy-2-butyn-1-one Using the method of Step C of Example 22, the compound of Step A was reacted to obtain a 1-(6-ethyl-7-methoxy-5-methylimidazol[1,2-a]pyrimidin-2-yl)-4-hydroxy-2-butyn-1-one.

EXAMPLES 24 TO 28

Using the methods of Step A or B of Example 1, the corresponding compounds of formula II or $I_A$ respectively were reacted to obtain the compounds of Examples 24 to 28. The yield, melting point and analytical data of compounds of formula I are given in Tables 1 to 4.

EXAMPLE 24

(3-bromo 6-ethyl 7-methoxy 5-methylimidazo[1,2-a]pyrimidin-2-yl) (propyn-1-ynyl)methanone

EXAMPLE 25

(3-bromoimidazo[1,2-a]pyridin-2-yl)isopropenyl methanone (chlorohydrate)

EXAMPLE 26

(imidazo[1,2-a]pyridin-2-yl)isopropenyl methanone

EXAMPLE 27

(imidazo [1,2-a]pyridin-2-yl) (2-phenylethyn-1-yl)methanone

EXAMPLE 28

3-bromoimidazo[1,2-a]pyridin-2-yl (2-phenylethyn-1-yl)methanone

TABLE A

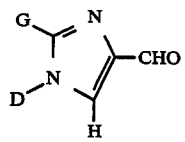

| PREP | G | D | Yield (%) | IR (KBr disc) (cm$^{-1}$) | M.p. (°C.) | Formula | M.W. | Theory/Found (%) C | H | N |
|---|---|---|---|---|---|---|---|---|---|---|
| A | MeS | –C₆H₄–OMe | 49 | 3130, 1690, 1670 | 118–20 | $C_{12}H_{12}N_2O_2S$ | 248.3 | 58.05 / 57.65 | 4.87 / 4.88 | 11.28 / 11.09 |
| B | MeS | –C₆H₄–Et | 80 | 3130, 1668, 1650 | 88–90 | $C_{13}H_{14}N_2OS$ | 246.3 | 63.39 / 63.44 | 5.73 / 5.73 | 11.37 / 11.41 |
| C | MeS | –C₆H₄–Me | 83 | 1680 | 111–3 | $C_{12}H_{12}N_2OS$ | 232.3 | | | |
| D | iPrS | –C₆H₄–Me | 75 | 1670 | 63–4 | $C_{14}H_{16}N_2OS$ | 260.3 | | | |
| E | MeS | –C₆H₄–F | 90 | 1690, 1675 | 130–1 | $C_{11}H_9FN_2OS$ | 236.3 | | | |

TABLE B

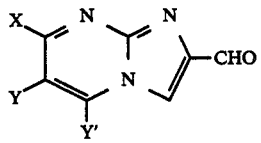

| PREP | X | Y | Y' | Yield (%) | IR (KBr disc) (cm$^{-1}$) | M.p. (°C.) | Formula | M.W. | Theory/Found (%) C | H | N | S |
|---|---|---|---|---|---|---|---|---|---|---|---|---|
| F | MeO | Et | Me | 72 | 3120, 3000, 2980, 2950, 1690, 1640 | 185–6 | $C_{11}H_{13}N_3O_2$ | 219.2 | 60.26 59.97 | 5.98 5.97 | 19.17 19.05 | |
| G | MeS | Et | Me | 85 | 3098, 2960, 2915, 2860, 1675, 1610 | 203–4 | $C_{11}H_{13}N_3OS$ | 235.3 | 56.15 56.35 | 5.58 5.58 | 17.85 17.95 | 13.63 13.34 |

TABLE C

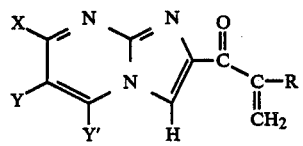

| PREP | X | Y | Y' | R | Yield (%) | IR (KBr disc) (cm$^{-1}$) | M.p. (°C.) | Formula | M.W. | Theory/Found (%) C | H | N | S |
|---|---|---|---|---|---|---|---|---|---|---|---|---|---|
| H | MeS | Et | Me | Me | 76 | 2970, 1630, 1615 | 136–7 | $C_{14}H_{17}N_3OS$ | 275.4 | 61.06 60.91 | 6.24 6.22 | 15.25 15.17 | 11.64 11.54 |
| J | MeO | Et | Me | Me | 35 | 3130, 1640 | 148–50 | $C_{14}H_{17}N_3O_2$ | 259.3 | 64.85 64.67 | 6.61 6.57 | 16.20 16.12 | |
| K | MeO | H | Me | Me | 56 | 3150, 2980, 2950, 1625 | 151 | $C_{12}H_{13}N_3O_2$ | 231.25 | 62.32 62.20 | 5.68 5.70 | 18.16 18.14 | |

TABLE 1

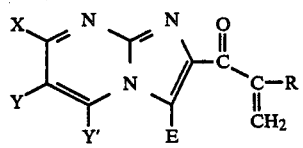

| Ex | X | Y | Y' | E | R | Method | Yield (%) | IR (KBr disc) (cm$^{-1}$) | M.p. (°C.) | Formula | M.W. | Theory/Found (%) C | H | N | Hal | S |
|---|---|---|---|---|---|---|---|---|---|---|---|---|---|---|---|---|
| 1 | MeS | Et | Me | Br | Me | B | 87 | 2960, 2920, 1640, 1600 | 87–9 | $C_{14}H_{16}BrN_3OS$ | 354.3 | 47.46 47.32 | 4.56 4.56 | 11.86 11.82 | 22.55(Br) 22.54 | 9.05 9.02 |
| 2 | MeO | Et | Me | Br | Me | B | 87 | 2960, 1635, 1625 | 101–2 | $C_{14}H_{16}BrN_3O_2$ | 338.2 | 49.71 49.73 | 4.78 4.72 | 12.42 12.31 | 23.63(Br) 23.67 | |
| 3 | MeO | Et | Me | Cl | Me | B | 62 | 2965, 1625 | 111–2 | $C_{14}H_{16}ClN_3O_2$ | 293.8 | 57.24 57.03 | 5.50 5.49 | 14.30 14.25 | 12.07(Cl) 12.17 | |
| 4 | MeO | H | Me | Br | Me | B | 98 | 3070, 2950, 1630 | 145–6 decomp | $C_{12}H_{12}BrN_3O_2$ | 310.15 | | | | | |
| 5 | MeO | Et | Me | Br | H | B | 47 | 2970, 2940, 2875, 1670, 1625 | 120–3 decomp | $C_{13}H_{14}BrN_3O_2$ | 324.2 | 48.16 48.05 | 4.36 4.32 | 12.96 12.73 | 24.65(Br) 24.45 | |

TABLE 2

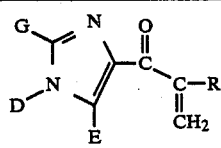

| Example | G | D | E | R | Method | Yield (%) | M.p. (°C.) IR (KBr disc) (cm$^{-1}$) | Formula | M.W. | Theory/Found (%) C | H | N | S | Other |
|---|---|---|---|---|---|---|---|---|---|---|---|---|---|---|

TABLE 2-continued

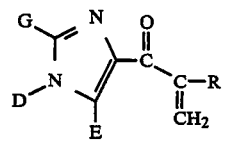

| Example | G | D | E | R | Method | Yield (%) | IR (cm⁻¹) | M.p. (°C.) | Formula | M.W. | Theory/Found (%) C | H | N | S | Other |
|---|---|---|---|---|---|---|---|---|---|---|---|---|---|---|---|
| 6 | MeS | –⟨⟩–Et | H | Me | A | 43 | 3120,1636, 1626,1611 | 46–7 | $C_{16}H_{18}N_2OS$ | 286.4 | 67.10 67.18 | 6.33 6.24 | 9.78 9.77 | 11.19 11.23 | |
| 7 | MeS | –⟨⟩–Et | Br | Me | B | 77 | 1636,1620 | 94–6 | $C_{16}H_{17}BrN_2OS$ | 365.3 | 52.61 52.62 | 4.69 4.69 | 7.67 7.67 | | |
| 8 | MeS | –⟨⟩–OMe | Br | $CH_3$ | B | 84 | 1630,1620, 1605 | 128–9 | $C_{15}H_{15}BrN_2O_2S$ | 367.3 | 49.05 48.86 | 4.12 4.10 | 7.63 7.55 | | 21.76 (Br) 21.74 |
| 9 | MeS | –⟨⟩–OMe | Cl | $CH_3$ | B | 93 | 1630,1620, 1600 | 110–1 | $C_{15}H_{15}ClN_2O_2S$ | 322.8 | 55.81 55.12 | 4.68 4.74 | 8.68 8.53 | | 10.98 (Cl) 11.39 |
| 10 | MeS | –⟨⟩–Me | Br | $CH_3$ | B | 52 | 1630,1610 | 89–90 | $C_{15}H_{15}BrN_2OS$ | 351.3 | 51.29 51.09 | 4.30 4.29 | 7.98 7.89 | | 22.75 (Br) 22.83 |
| 11 | iPrS | –⟨⟩–Me | Br | $CH_3$ | B | 66 | 1635,1615, 1605 | 135–6 | $C_{17}H_{19}BrN_2OS$ | 379.3 | 53.83 53.76 | 5.05 5.07 | 7.39 7.33 | | 8.45 (S) 8.43 |
| 12 | MeS | –⟨⟩–F | Br | $CH_3$ | B | 75 | 1635,1595 | 99–101 | $C_{14}H_{12}BrFN_2OS$ | 355.2 | 47.33 47.37 | 3.41 3.48 | 7.81 7.81 | | 9.02 (S) 9.05 |
| 13 | MeS | –⟨⟩–OMe | Br | H | B | 68 | 1655,1600 | 117–9 | $C_{14}H_{13}BrN_2O_2S$ | 353.2 | 47.60 47.36 | 3.71 3.75 | 7.93 7.79 | | 22.62 (Br) 22.72 |
| 14 | MeS | –⟨⟩–OH | Br | $CH_3$ | B | 86 | 3220,1610, 1590 | 159–61 | $C_{14}H_{13}BrN_2O_2S$ | 353.2 | 47.60 47.63 | 3.71 3.72 | 7.93 7.82 | | |
| 15 | iPrS | Et | Br | $CH_3$ | B | 53 | 2960,1635, 1590 | oil | $C_{12}H_{17}BrNO_2S$ | 317.2 | 45.43 44.98 | 5.40 5.37 | 8.83 8.69 | | |
| 16 | iPrSO | –⟨⟩–Et | Cl | $CH_3$ | C | 41 | 1640,1610, 1595 | 83–4 | $C_{18}H_{21}ClN_2O_2S$ | 364.8 | | | | | |
| 17 | EtSO | –⟨⟩–Et | Cl | $CH_3$ | C | 33 | 1640,1610, 1600 | 76–8 | $C_{17}H_{19}ClN_2O_2S$ | 350.8 | | | | | |

TABLE 3

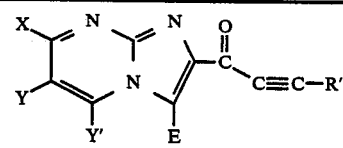

| Ex | X | Y | Y' | E | R' | Method | Yield (%) | IR (cm⁻¹) | M.p. (°C.) | Formula | M.W. | Theory/Found (%) C | H | N | Hal |
|---|---|---|---|---|---|---|---|---|---|---|---|---|---|---|---|
| 18 | MeO | Et | Me | H | Ph | A | 86 | 2197,1630 | 194–6 | $C_{19}H_{17}N_3O_2$ | 319.4 | 71.46 71.33 | 5.37 5.42 | 13.16 13.11 | |
| 19 | MeO | Et | Me | H | t-Bu | A | 71 | 2965,2215, 1635 | 133–5 | $C_{17}H_{21}N_3O_2$ | 299.3 | 68.21 68.19 | 7.07 7.09 | 14.04 14.06 | |
| 20 | MeO | Et | Me | Br | t-Bu | B | 86 | 2970,2930, 2870,2200, | 186–7 | $C_{17}H_{20}BrN_3O_2$ | 378.3 | 53.97 53.72 | 5.34 5.33 | 11.10 10.97 | 21.12(Br) 20.89 |

TABLE 3-continued

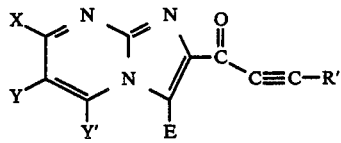

| Ex | X | Y | Y' | E | R' | Method | Yield (%) | IR (cm$^{-1}$) | M.p. (°C.) | Formula | M.W. | C | H | N | Hal |
|---|---|---|---|---|---|---|---|---|---|---|---|---|---|---|---|
| | | | | | | | | | | | | \multicolumn{4}{c|}{Theory/Found (%)} |
| 21 | MeO | Et | Me | Br | Ph | B | 79 | 1640,1620 3050,2960, 2920,2200, 1630 | 187–190 | $C_{19}H_{16}BrN_3O_2$ | 398.3 | 57.30 57.24 | 4.06 4.09 | 10.55 10.45 | 20.06(Br) 20.11 |
| 22 | MeO | Et | Me | H | —CH$_2$OH | A | 41 | 3400,3125, 2210,1635 | 176–186 (decomp) | $C_{14}H_{15}N_3O_3$ | 273.3 | 61.53 | 5.53 | 15.38 | |
| 23 | MeO | Et | Me | Br | —CH$_2$OH | B | 28 | 3250,2980, 2880,2220, 1630 | 212–3 (decomp) | $C_{14}H_{14}BrN_3O_3$ | 352.2 | 47.74 47.63 | 4.01 4.08 | 11.93 11.78 | 22.69(Br) 22.36 |
| 24 | MeO | Et | Me | Br | CH$_3$ | B | 93 | 2960,2230, 2205,1630 | 170–2 (decomp) | $C_{14}H_{14}BrN_3O$ | 320.2 | 52.51 | 4.42 | 13.12 | 24.96(Br) |

TABLE 4

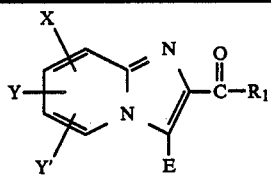

| Ex | X | Y | Y' | E | R$_1$ | Method | Yield (%) | IR (cm$^{-1}$) | M.p. (°C.) | Formula | M.W. | C | H | N | Hal |
|---|---|---|---|---|---|---|---|---|---|---|---|---|---|---|---|
| | | | | | | | | | | | | \multicolumn{4}{c|}{Theory/Found (%)} |
| 25 | H | H | H | Br | —CMe=CH$_2$ | B | 79 | 3070, 2540, 1650 | 140–2 (HCl salt) | $C_{11}H_9BrN_2O$ | 301.6 | 43.81 43.57 | 3.35 3.41 | 9.28 9.11 | |
| 26 | H | H | H | H | —CMe=CH$_2$ | A | 77 | 3145, 3100, 3080, 3040, 1635 | 93–4 | $C_{11}H_{10}N_2O$ | 186.2 | 70.95 71.08 | 5.42 5.40 | 15.04 15.03 | |
| 27 | H | H | H | H | —C≡C—Ph | A | 80 | 3140, 3100, 3080, 3050, 2190, 1630 | 168 | $C_{16}H_{10}N_2O$ | 246.3 | 78.03 77.96 | 4.10 4.23 | 11.37 11.31 | |
| 28 | H | H | H | Br | —C≡C—Ph | B | 74 | 3080, 3050, 2200, 1630 | 133–4 | $C_{16}H_9BrN_2O$ | 325.15 | 59.10 59.01 | 2.80 2.92 | 8.61 8.60 | 24.57(Br) 24.66 |

EXAMPLE 29

Tablets containing 20 mg of the compound of Example 1 or 7 and sufficient excipient of lactose, starch, talc and magnesium stearate for a final tablet weight of 100 mg were prepared.

BIOCHEMICAL ACTIVITY

The inhibition of ionophore-stimulated release of free arachidonic acid from [$^{14}$C]-arachidonic acid pre-labelled rat peritoneal neutrophils was studied using modifications of the method of Ahnfelt-Ronne and Arrigoni-Martelli [Biochemical Pharmacol., (1982) Vol. 31, p. 2619]. The results below show the micromolar concentrations of test compound required to inhibit, by 50% compared to controls, the release of radiolabelled products into supernatant liquid (IC$_{50}$-μM).

| Example | IC$_{50}$ - μM |
|---|---|
| 1 | 6.8 |
| 2 | 17 |
| 3 | 21 |
| 4 | 7.4 |
| 5 | 1.7 |
| 6 | 3.8 |
| 7 | 2.5 |
| 8 | 7.2 |
| 9 | 9.1 |
| 10 | 10 |
| 11 | 3.7 |
| 12 | 15 |
| 13 | 2.3 |
| 14 | >10 |
| 15 | 17 |
| 16 | 4.4 |
| 17 | — |
| 18 | 12 |
| 19 | 16 |
| 20 | 4.2 |
| 21 | 1.5 |
| 22 | 59 |
| 23 | 46 |
| 24 | 7.2 |
| 25 | 28 |
| 26 | >100 |
| 27 | 41 |
| 28 | 5.2 |

Various modifications of the compounds and methods of the invention may be made without departing from the spirit or scope thereof and it is to be understood that the invention is intended to be limited only as defined in the appended claims.

What we claim is:

1. A compound selected from the group consisting of compounds of the formula

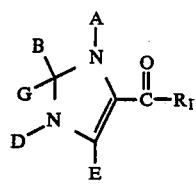

wherein $R_1$ is selected from the group consisting of

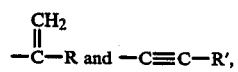

R is selected from the group consisting of hydrogen and alkyl of 1 to 5 carbon atoms, R' is selected from the group consisting of hydrogen, alkyl and hydroxyalkyl of 1 to 5 carbon atoms, and aryl of 6 to 10 carbon atoms unsubstituted or substituted with at least one member of the group consisting of halogen, —OH, —COOH, $CF_3$ and alkyl and alkoxy of 1 to 5 carbon atoms, A and B together form a bond, G is selected from the group consisting of alkyl, alkoxy and alkylthio of 1 to 5 carbon atoms and alkylsulfinyl and alkylsulfonyl of 1 to 5 carbon atoms, D is selected from the group consisting of alkyl of 1 to 5 carbon atoms and phenyl unsubstituted or substituted with at least one member of the group consisting of halogen, —OH, —COOH, —$CF_3$ and alkyl and alkoxy of 1 to 5 carbon atoms and E is hydrogen or halogen and its non-toxic, pharmaceutically acceptable acid addition salts.

2. A compound of claim 1 wherein E is halogen.

3. A compound of claim 1 wherein A and B taken together are a bond, G is alkylthio of 1 to 5 carbon atoms and D is phenyl unsubstituted or substituted with at least one member of the group consisting of halogen, —OH, —COOH, —$CF_3$ and alkyl and alkoxy of 1 to 5 carbon atoms.

4. A compound of claim 1 selected from the group consisting of
1-[5-bromo-1-(4-ethylphenyl)-2-methylthioimidazol-4-yl]-2-methyl-2-propen-1-one; and
1-[5-bromo-1-(4-methoxyphenyl)-2-methylthioimidazol-4-yl]-2-propen-1-one;
and their non-toxic, pharmaceutically acceptable acid addition salts.

5. An anti-inflammatory composition comprising an anti-inflammatorily effective amount of at least one compound of claim 1 and an inert pharmaceutical carrier.

6. A composition of claim 5 wherein E is halogen.

7. A composition of claim 5 wherein A and B taken together are a bond, G is alkylthio of 1 to 5 carbon atoms and D is phenyl unsubstituted or substituted with at least one member of the group consisting of halogen, —OH, —COOH, —$CF_3$ and alkyl and alkoxy of 1 to 5 carbon atoms.

8. A composition of claim 5 wherein the active compound is selected from the group consisting of
1-[5-bromo-1-(4-ethylphenyl)-2-methylthioimidazol-4-yl]-2-methyl-2-propen-1-one; and
1-[5-bromo-1-(4-methoxyphenyl)-2-methylthioimidazol-4-yl]-2-propen-1-one;
and their non-toxic, pharmaceutically acceptable acid addition salts.

9. A method of relieving inflammation in warm-blooded animals comprising administering to warm-blooded animals in anti-inflammatorily effective amount of at least one compound of claim 1.

10. A method of claim 9 wherein E is halogen.

11. A method of claim 9 wherein A and B taken together are a bond, G is alkylthio of 1 to 5 carbon atoms and D is phenyl unsubstituted or substituted with at least one member of the group consisting of halogen, —OH, —COOH, —$CF_3$ and alkyl and alkoxy of 1 to 5 carbon atoms.

12. A method of claim 9 wherein the active compound is selected from the group consisting of
1-[5-bromo-1-(4-ethylphenyl)-2-methylthioimidazo-4-yl]-2-methyl-2-propen-1-one; and
1-[5-bromo-1-(4-methoxyphenyl)-2-methylthioimidazol-4-yl]-2-propen-1-one; and their non-toxic, pharmaceutically acceptable acid addition salts.

* * * * *